United States Patent [19]

Kaiser

[11] Patent Number: 4,967,775
[45] Date of Patent: Nov. 6, 1990

[54] TRANSPARENT SAFETY GUARD FOR MANICURIST USE

[76] Inventor: Carol M. Kaiser, 1502 Suydam Rd., Sandwich, Ill. 60548

[21] Appl. No.: 374,591

[22] Filed: Jun. 29, 1989

Related U.S. Application Data

[63] Continuation of Ser. No. 193,070, May 12, 1988, abandoned.

[51] Int. Cl.⁵ .............................................. A45D 29/00
[52] U.S. Cl. .............................................. 132/73; 2/11
[58] Field of Search ................ 132/73, 73.5, 319, 333; 2/11, 16, 161 R, 167

[56] References Cited

U.S. PATENT DOCUMENTS 2,218,296 10/1940 Perras .................................... 132/73
4,400,829 8/1983 Willis ........................................ 2/16

FOREIGN PATENT DOCUMENTS 0012188 of 1900 United Kingdom ...................... 2/16

Primary Examiner—John J. Wilson
Assistant Examiner—Adriene B. Lepiane
Attorney, Agent, or Firm—Dressler, Goldsmith, Shore, Sutker & Milnamow, Ltd.

[57] ABSTRACT

A transparent safety guard for use by manicurists. The safety guard includes an elongate concave flaring transparent shield securable to the wrist or ankle of a customer so that fingernail and toenail clippings which would otherwise propel towards the eyes of the manicurist or customer are prevented from doing so.

4 Claims, 1 Drawing Sheet

TRANSPARENT SAFETY GUARD FOR MANICURIST USE

This application is a continuation of application Ser. No. 07/193,070, filed May 12, 1988, and abandoned June 29, 1989.

BACKGROUND OF THE INVENTION

This invention relates to a safety guard for use by a customer for protecting the customer and a manicurist.

Manicurists and customers are routinely threatened by flying clippings which are propelled in all directions as fingernails and toenails are cut. These sometimes strike manicurists and customers in the eye, sometimes resulting in injury. Liability insurance to cover such injuries is therefore needed, increasing the cost of conducting manicuring operations.

In recent years that problem has increased with the widespread use of augmented fingernails with added plastic and other overlays. This has made fingernails thicker and tougher and more difficult to cut, and has increased the size and weight of clippings, the distance clippings are projected, and the force with which they are projected, as they are severed by clippers used by manicurists.

It would be desirable to diminish the possibility of injury to manicurists and customers, and the development of the present invention accomplishes that goal.

SUMMARY OF THE INVENTION

The present invention comprises a transparent safety guard for manicurist use. The transparent safety guard includes an elongate, concave transparent shield portion having a first end of diminished size and a second flared, enlarged end, and a securing means for securing the first end to a human wrist or ankle.

The securing means comprises a band secured to the first end and, with said first end, is adapted to removably embrace a wrist or ankle to temporarily secure the shield to a wrist or ankle against removal. The transparent shield is formed into a concave configuration which flaringly enlarges in size in plan view from the first end to the second end, and which is sized to overlie the length of a hand or foot, and to accommodate the width of a hand or foot and as well as the vertical height of an extended hand or foot. The second end of the shield is sized to extend beyond the tips of the fingers or toes of the person to whose wrist or ankle the band is secured. With such a safety guard, as a manicurist clips the nails of a user, flying clippings hit the shield instead of propelling upwardly at the manicurist or user.

In a preferred form the band comprises a fabric fastening means of loops and piles, and the shield is preformed in a concave configuration. The shield may flare gradually and continuously from adjacent the first end to the second end.

Further objects, features and advantages of the present invention will become apparent from the following description and drawings.

DESCRIPTION OF A PRESENTLY PREFERRED EMBODIMENT

Figure 1:
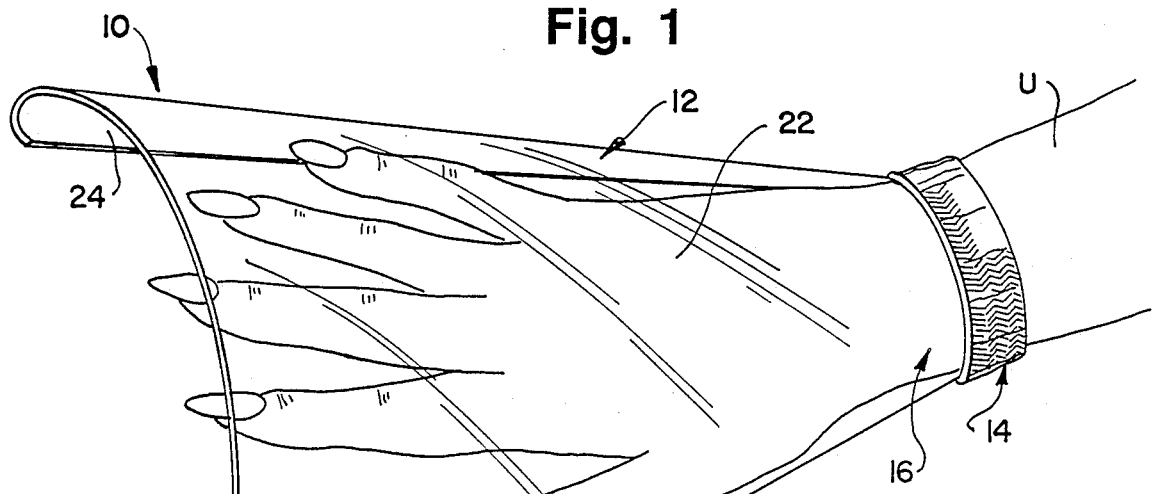
FIG. 1 is a top perspective view of a guard of the present invention.
Figure 4:
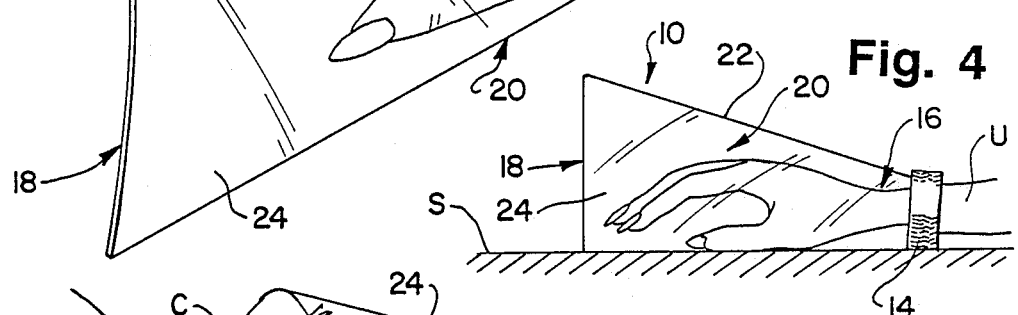
FIG. 4 is a side elevational view of a nail guard of the present invention.

Referring now to the drawings, a nail safety guard 10 of the present invention comprises a transparent shield 12 and a securing means 14. Although the safety guard may be formed and used for both the manicuring of fingernails and toenails, or in slightly different forms for one or the other, the drawings illustrate, and this description will describe, the use and specific configuration of a safety guard 10 especially adapted for fingernail manicuring.

Figure 2:
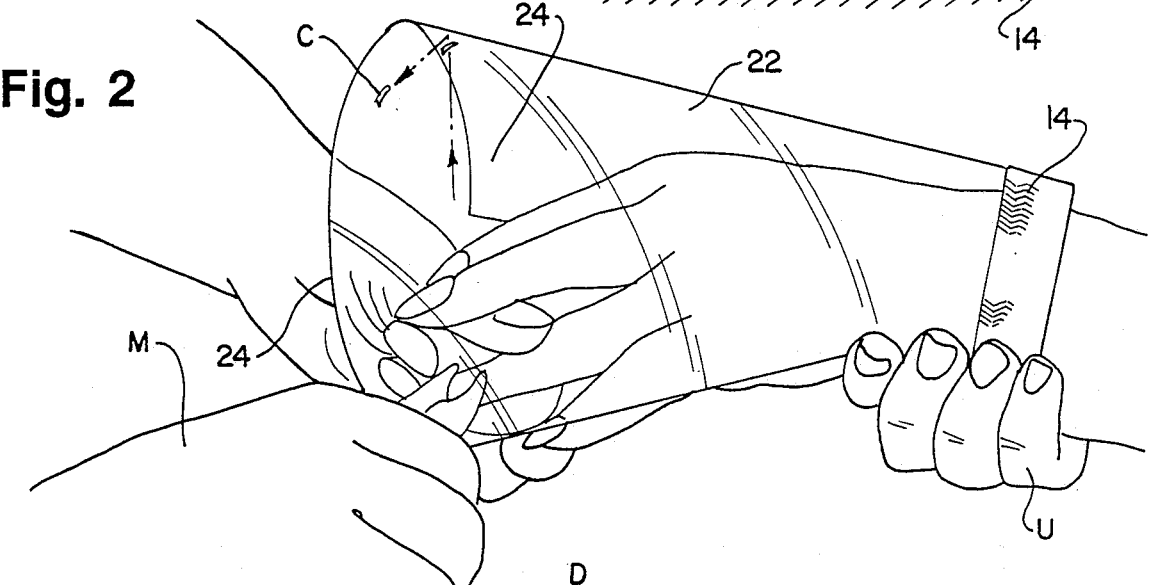
FIG. 2 is a view of a nail guard of the present invention in use.
Figure 3:
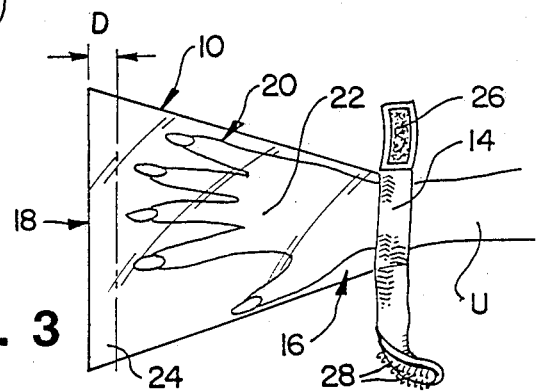
FIG. 3 is a plan view of a nail guard of the present invention.

As best seen in FIG. 2, the shield 12 terminates at a first end 16 adjacent the wrist of a user/customer U. The first end 16 is curved into a concave configuration of a first diminished size proportioned to comfortably receive the wrist of an average user and to partially encircle the wrist. The shield then flaringly enlarges in size in plan view from the first end towards a second flared enlarged end 18. In plan view the intermediate portions 20 of the shield 12 are narrower than the second end and wider than the first end. Although the flare may be progressive from the first end to the second end, of course the first end might be more cylindrical or cuff-like, and the flare may therefore commence intermediate the ends and need not, for that matter, be of uniform progression from its zone of commencement adjacent the first end.

As may be seen in the drawings, not only does the shield flaringly enlarge between its ends, but it is also concave in configuration, thereby to provide a top portion 22 which is a transparent surface which protects the user and the manicurist M, and which also makes it possible for the manicurist to see the customer's hand clearly. The sides or side portions 24 also serve a protective function. The side portions 24 may have a sufficient vertical or side elevational dimension so that one or both of them may engage a table surface S when the user is being manicured. In any event their vertical or side elevational dimension is sufficient so that when a hand being manicured is in a gently cupped repose, and/or is being supported in such repose by a manicurist's hand (as seen in FIG. 2), clippings C which are propelled outwardly at an angle which might direct them at the eyes of a user or manicurist, engage the top portion 22 or the side portions 24.

Thus, the shield is of a concave configuration which is sufficient to accommodate both the width of a hand and fingers and the vertical height of a hand and fingers when in a fully extended position as well, of course, as when hands are in a cupped gentle repose. The shield is also of a length sufficient to overlie and project forwardly a distance D beyond the tips of the fingers of a user so that clippings which propel upwardly or outwardly towards the manicurist may not fly outwardly at an angle which will strike the manicurist in the face.

The securing means 14 may take a variety of forms. Its principal purpose is to secure the first end of the shield to a wrist or ankle. In a preferred embodiment the securing means comprises a Velcro fabric bracelet secured, as by adhesive, to the first end 16 with free ends, one of conventional loops 26 and one of conventional hooks 28 for engagement to provide an encircling bracelet of a size to accommodate the wrist of the user. Ties, conformable bracelets, and other securing means may be used as well, and the securing means and rigidity or flexibility of movement of the first end 14 relative to the user may vary, especially where the shield is one which is intended for interchangeable use for foot and hand manicures.

It may well be desirable to provide safety shields in several sizes to accommodate to different hand sizes. Thus, for those customers with small hands, it may be desirable to provide a shield of a lesser length in plan view for convenience of manicurist use, and for those with longer hands, a shield of a greater length in plan view may be used to secure the benefits of the invention. Of course a longer shield may be used as a universal shield by moving the first end rearwardly of the wrist for users with smaller hands.

Clearly variations in dimensions, concavity, flare and the like may be employed without departing from the spirit and scope of the invention. Accordingly, the invention is not to be considered as being limited, except insofar as may be dictated by the claims.

What is claimed is:

1. A transparent safety guard for manicurist and like use comprising, an elongate, concave transparent shield having a first end of diminished size and a second flared, enlarged end, and securing means for securing the first end to a human wrist or ankle, said shield being self-supporting and being without a supporting base, said securing means comprising a band secured with said first end and which is adapted to removably embrace a wrist or ankle to temporarily secure said shield to a said wrist or ankle against removal, said transparent shield being formed into a concave configuration which flaringly enlarges in size both in plan view and in side view from said first end to said second end and which is sized to overlie a hand or foot and to accommodate the width of a hand or foot and the vertical height of a hand or foot when extended, the second end of which is sized to extend beyond the extended tips of the fingers or toes of the person to whose wrist or ankle the band is secured, said shield having side portions which are adapted to engage and to support the shield on a table surface while providing a front access zone for a manicurist, whereby as a manicurist clips the nails of a user, flying clippings hit the shield instead of propelling upwardly or sidewardly at the manicurist or user.

2. A transparent safety guard in accordance with claim 1, and wherein said band comprises a fabric fastening means of loops and pile.

3. A transparent safety guard in accordance with claim 1, and wherein said shield is preformed in a concave configuration.

4. A transparent safety guard in accordance with claim 1, and wherein said shield flares gradually and continuously from adjacent said first end to said second end.

* * * * *